US005716982A

United States Patent [19]

Han et al.

[11] Patent Number: 5,716,982
[45] Date of Patent: Feb. 10, 1998

[54] RETINOIDS AND METHODS OF USE OF SAME

[75] Inventors: Rui Han; Shi-Ping Xu, both of Beijing, China

[73] Assignee: Institute of Materia Medica, an institute of the Chinese Academy of Medical Sciences, Beijing, China

[21] Appl. No.: 487,061

[22] Filed: Jun. 7, 1995

[51] Int. Cl.$^6$ .................. C07D 311/12; C07D 311/14; C07D 311/16; A61K 31/37

[52] U.S. Cl. .............. 514/457; 549/283; 549/285; 549/287; 549/289; 514/261; 544/277

[58] Field of Search .................. 549/283, 285, 549/287, 289; 514/457

[56] References Cited

U.S. PATENT DOCUMENTS

| | | | |
|---|---|---|---|
| 3,541,097 | 11/1970 | Beyerle et al. | 544/364 |
| 4,126,693 | 11/1978 | Gander et al. | 514/466 |
| 4,144,336 | 3/1979 | Boltze et al. | 514/232.5 |
| 4,151,179 | 4/1979 | Appleton et al. | 549/401 |
| 4,190,594 | 2/1980 | Gander et al. | 554/35 |
| 4,310,546 | 1/1982 | Gander | 514/549 |
| 4,323,581 | 4/1982 | Gander | 514/613 |
| 4,385,175 | 5/1983 | Just et al. | 540/300 |
| 4,523,042 | 6/1985 | Loev et al. | 568/824 |
| 4,602,034 | 7/1986 | Briet et al. | 514/456 |
| 4,713,465 | 12/1987 | Kramer et al. | 549/403 |
| 4,783,533 | 11/1988 | Briet et al. | 514/456 |
| 4,960,908 | 10/1990 | Ito et al. | 549/403 |
| 5,096,713 | 3/1992 | Philippe et al. | 424/427 |
| 5,096,924 | 3/1992 | Ishizuka et al. | 514/456 |
| 5,116,954 | 5/1992 | Briet et al. | 534/551 |
| 5,124,083 | 6/1992 | Shealy | 514/529 |
| 5,141,746 | 8/1992 | Fleury et al. | 424/195.1 |

FOREIGN PATENT DOCUMENTS 1127170  7/1982  Canada .

OTHER PUBLICATIONS

Shiping Xu et al., CA 96:123037, 1982.
Shiping Xu et al., Yaoxue Xerbao (1981), 16(9), 678–86.
S. Shibata, *Anti–tumorgenic chalcones*, Stem Cells, vol. 12:44–62, 1994.
Srivastava et al. *Effect of quercetin on serine/threonine and tyrosine protein kinase*, Plant Flavonoids in Biology and Medicine: Biochemical, Pharmacological and Structure–Activity Relationships, pp. 315–318, 1986.
Piantelli et al. *Type II Estrogen Binding Sites and Antiproliferative Activity of Quercetin in Human Meningiomas*, Cancer, vol. 71:193–199, 1993.
B. Havsteen, *Flavonoids, A Class of Natural Products of High Pharmacological Potency*, Biochemical Pharmacology, vol. 32:1141–1148, 1983.
Chae et al. *Effects of synthetic and naturally occurring flavonoids on benzo[a]pyrene metabolism by hepatic microsomes prepared from rats treated with cytochrome P–450 inducers*, Cancer Letters, vol. 60, pp. 15–24, 1991.

M.E. Marshall et al. Growth–inhibitory effects of coumarin (1,2–benzopyrone) and 7–hydroxycoumarin on human malignant cell lines in vitro, J. Cancer Res. & Clin. Oncol., vol. 120, pp. S3–S10, 1994.
Bibby et al. *Flavone acetic acid–from laboratory to clinic and back*, Anti–Cancer Drugs, vol. 4, pp. 3–17, 1993.
Jing et al. *Structural Requirements for Differentiation–Induction and Growth–Inhibition of Mouse Erythroleukemia Cells by Isoflavones*, Anticancer Research, vol. 15, pp. 1147–1152, 1995.
Blazsek et al., *Retinoic acid in mono–or combined differentiation therapy of myelodysplasia and acute promyelocytic leukemia*, Biomed & Pharmacother, vol. 45, pp. 169–177, 1991.
Abstract—Cassady et al., *Recent Advances in the Discovery of Potential Cancer Chemopreventive Agents*, Abstract Collection of International Symposium on Recent Advances in Chemistry and Molecular Biology of Cancer Research, Beijing, China, pp. 5–6, 1991.
Castaigne et al., *All–Trans Retinoic Acid as a Differentiation Therapy for Acute Promyelocytic Leukemia. I. Clinical Results*, Blood, vol. 76, No. 9, pp. 1704–1709, 1 Nov. 1990.
Chomienne et al., *All–Trans Retinoic Acid in Acute Promyelocytic Leukemias. II. In Vitro Studies: Structure–Function Relationship*, Blood, vol. 76, No. 9, pp. 1710–1717, 1 Nov. 1990.
Chomienne et al., *Structure–Activity Relationships of Aromatic Retinoids on the Differentiation of the Human Histiocytic Lymphoma Cell Line U–937*, Leukemia Research, vol. 10, No. 11, pp.1301–1305, 1986.
Clarkson, *Retinoic Acid in Acute Promyelocytic Leukemia: The Promise and the Paradox*, Cancer Cells, vol. 3, No. 6, pp. 211–220, Jun. 1991.
Dawson et al., *Aromatic Retinoic Acid Analogues. Synthesis and Pharmacological Activity*, Journal of Medicinal Chemistry, vol. 24, No. 5, pp. 583–592, 1981.
Dawson et al., *Conformationally Restricted Retinoids*, J. Med. Chem., vol. 27, No. 11, pp. 1516–1531, 1984.
Degos, *All–trans retinoic acid (ATRA) therapeutical effect in acute promyelocytic leukemia*, Biomed & Pharmacother, vol. 46, pp. 201–209, 1992.
Abstract—Du et al., *Comparison of Toxicities of 4–(ethoxycarbophenyl) Retinamide and Some Other Retinoids*, Institute of Materia Medica, vol. 18, No. 5, 1982.
Edwards et al., *Chalcones: A New Class of Antimitotic Agents*, J. Med. Chem., vol. 33, pp. 1948–1954, 1990.

(List continued on next page.)

*Primary Examiner*—Johann Richter
*Assistant Examiner*—Laura L. Stockton
*Attorney, Agent, or Firm*—Browdy and Neimark

[57]  ABSTRACT

New retinoid compounds, as coumarin retinoids and/or purine retinoids and compositions thereof, are provided which exhibit therapeutic and/or biological activity on cancer or precancer cells, as well as to methods of use of same.

5 Claims, 1 Drawing Sheet

OTHER PUBLICATIONS

Egan et al., *The Pharmacology, Metabolism, Analysis, and Applications of Coumarin and Coumarin–Related Compounds*, Drug Metabolism Reviews, vol. 22, No. 5, pp. 503–529, 1990.

Abstract—Han et al., *Effects of S86019, An Active Component From Puralia Lobata, On Cell Differentiation and Cell Cycle Traverse of HL–60 Cells*, Chinese Journal of Cancer Research, vol. 2, No. 3, pp. 51–53, 1990.

Han et al., *Evaluation of N–4–(Hydroxycarbophenyl) Retinamide as a Cancer Prevention Agent and as a Cancer Chemotherapeutic Agent*, In Vivo, vol. 4, pp. 153–160, 1990.

Harvey et al., *A New Coumarin Synthesis and Its Utilization for the Synthesis of Polycyclic Compounds with Anticarcinogenic Properties*, J. Org. Chem., vol. 53, No. 17, pp. 3936–3943, 1988.

Harvey et al., *A New Chromone and Flavone Synthesis and Its Utilization for the Synthesis of Potentially Antitumorigenic Polycyclic Chromones and Flavones*, J. Org. Chem., vol. 55, No. 25, pp. 6161–6166, 1990.

Abstract—Ho et al., *Synthesis and Structure—Activity Relationship of Potential Inhibitors of Benzo[a]pyrene Carcinogenesis*, Abstract Collection of International Symposium on Recent Advances in Chemistry and Molecular Biology of Cancer Research, Beijing, China, pp. 68–69, Jul. 1991.

Abstract—Jing et al., *Differentiation of B16 Melanoma Cells Induced by Daidzein*, Chinese Journal of Pharmacology and Toxicology, vol. 6, No. 4, pp. 278–280, Nov. 1992.

Kizaki et al., *Differentiation–Inducing Agents in the Treatment of Myelodysplastic Syndromes*, Seminars in Oncology, vol. 19, No. 1, pp. 95–105, Feb. 1992.

Kagechika et al., *Retinobenzioc Acids. 3. Structure–Activity Relationships of Retinoidal Azobenzene–4–carboxylic Acids and Stilbene–4–carboxylic Acids*, J. Med. Chem., vol. 32, pp.1098–1108, 1989.

LoCoco et al., *Molecular Evaluation of Response to All–Trans–Retinoic Acid Therapy in Patients With Acute Promyelocytic Leukemia*, Blood, vol. 77, No. 8, pp. 1657–1659, 15 Apr. 1991.

Middleton, Jr., *Effects of Flavonoids on Immune and Inflammatory Cell Functions*, Biochemcial Pharmacology, vol. 43, No. 6, pp. 1167–1179, 1992.

Nair et al., *Novel Coumarins as Potential Anticarcinogenic Agents*, Carcinogenesis, vol. 12, No. 1, pp. 65–69, 1991.

Newton et al., *Structure–Activity Relationships of Retinoids in Hamster Tracheal Organ Culture*, Cancer Research, vol. 40, pp. 3413–3425, Oct. 1980.

Preuss–Ueberschar et al., Drug Res., vol. 34, pp. 1305–1313, 1984.

Sato et al., *Functional Studies of Newly Synthesized Benzoic Acid Derivatives: Identification of Highly Potent Retinoid–Like Activity*, Journal of Cellular Physiology, vol. 135, pp. 179–188, 1988.

Shealy et al., *Terminal Bifunctional Retinoids. Synthesis and Evaluation Related to Cancer Chemopreventive Activity*, J. Med. Chem., vol. 31, pp. 1124–1130, 1988.

Skrede et al., *Retinyl Esters in Chylomicron Remnants Inhibit Growth of Myeloid and Lymphoid Leukaemic Cells*, European Journal of Clinical Investigation, vol. 21, pp. 574–579, 1991.

Smith et al., *Retinoids in Cancer Therapy*, Journal of Clinical Oncology, vol. 10, vo. 5, pp. 839–864, May 1992.

Abstract—Song et al., *Differentiation of Human Promyelocytic Leukemia (HL–60) Cells Induced By New Synthetic Retinoids 4–(ethoxycarbophenyl) Retinamide and 4–(hydroxycarbophenyl) Retinamide*, Institute of Materia Medica, Chinese Academy of Medical Sciences, pp. 576–581, 1984.

Warrell, Jr., *All–Trans–Retinoic Acid: What Is It Good For?* Journal of Clinical Oncology, vol. 10, No. 11, pp. 1659–1661, Nov. 1992.

RETINOIDS AND METHODS OF USE OF SAME

BACKGROUND OF THE INVENTION

1. Field of the Invention

The present invention relates to novel retinoids, as coumarin retinoids and/or purine retinoids, and compositions thereof, which exhibit therapeutic and/or biological activity on cancer or precancer cells, as well as to methods of using same.

2. Description of the Related Background Art

Retinoids play an important role in the development and differentiation of epidermal cells, as well as in reversing precancerous lesions. Clinical trials have been conducted using N-(4-carboxyphenyl) retinamide in the treatment of some precancerous lesions, oral leukoplakia, vulval leukoplakia, a typical dysplasia of the cervix and the gastric mucosa, and the like (Han et al., in vivo 4:153–160 (1990)). Other retinoids, such as isoretinoin and etretinate, are in current use as prescription drugs for the treatment of acne and psoriasis (Gander et al., U.S. Pat. No. 4,126,693).

However, retinoids have a significant level of toxicity, and treatment using known retinoid agents suffers from problems due to the level of toxicity and side effects which accompany administration of known retinoid compounds. Accordingly, there exists a need to provide novel compounds having retinoid activity but which have less toxicity and/or side effects.

Smith et al., *J. Clin. Oncol.* 10 (5):839–864 (1992), reviews the use of retinoids in cancer therapy with most of the emphasis on anti-tumor effects in patients with acute promyelocytic leukemia (APL). Smith et al. reports that the natural retinoid, all-trans-retinoic acid (RA),

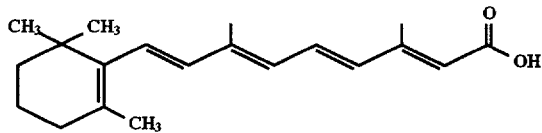

induces cell differentiation in some human acute myeloid leukemia (AML), neuroblastoma, teratocarcinoma, melanoma, and rat rhabdomyosarcoma cells and also appears to play an essential role in the normal differentiation of epithelial cells. Clinical toxicities associated with the use of RA in dermatologic studies are listed in Table 6 of the Smith et al. reference with disclosure in the text that retinoids are recognized as powerful teratogens.

Kizaki et al., *Seminars in Oncology* 19 (1):95–105 (1992), reports that retinoids are potent anti-carcinogenic agents in many experimental models and that they inhibit growth and induce differentiation of transformed neoplastic cells. A number of references specifically relate to retinoic acid derivatives as anti-cancer agents. Just et al., U.S. Pat. No. 4,385,175, discloses esters of retinoic acid with azetidinones useful as anti-cancer agents. Philippe et al., U.S. Pat. No. 5,096,713, discloses retinoic esters of L-cladinose which exhibit anti-tumor activity. The Paust Canadian Patent No. 1,127,170, is specifically directed to retinic acid N-(carboxy)-phenylamindes and 7,8-dehydro-retinic acid N-(carboxy)-phenylamides, and discloses that, while the retinic compounds are predominantly directed toward preventing cancer, they may be used for therapeutic treatment of tumors of the bladder, the mammary gland, the skin and the mucous membranes.

A number of references disclose retinoids being used in cancer prophylaxis and as inducers of cell differentiation. For instance, Newton et al., *Cancer Res.* 40:3413–3425 (1980) discloses a long list of esters, amines and amides of retinoic acid and their activity in cancer prophylaxis. None of the listed compounds are related to flavonoids or chalcone retinoids. Duet al., *Inst. Mater. Med. Chinese Acad. Med. Sci. Beijing* 17:331–337 (1982), discloses the retinamides $R_{II}$ (N-4(hydroxycarbophenyl) retinamide) and $R_I$ (4-(ethoxycarbyl-phenyl) -retinamide) and their utility as cancer preventatives. Song et al., *Inst. Mater. Med. Chinese Acad. Med. Sci. Beijing* 19:576–581 (1984), also relates to the property of the retinamides $R_I$ and $R_{II}$ as cell differentiation inducers. The Shealy patent, U.S. Pat. No. 5,124,083, discloses derivatives of retinoic acid as cell differentiation agents for cancer prevention and treatment and the Shealy et al. publication, *J. Med. Chem.* 31:1124–1130 (1988), discloses the chemopreventative activity of bifunctional retinoic acid esters. Dawson, *J. Med. Chem.* 27:1516–1531 (1984), Dawson et al., *J. Med. Chem.* 27:583–592 (1981), Kagechika et al., *J. Med. Chem.* 32:1098–1108 (1989), Skrede et al., *Eur. J. Clin. Investig.* 21:574–579 (1991) and Loev et al., U.S. Pat. No. 4,523,042, all disclose various retinoid compounds which are cell differentiation agents. Gander, U.S. Pat. No. 4,323,581, discloses the use of N-(4-hydroxyphenyl)-all-transretinamide for treatment of breast cancer while in U.S. Pat. No. 4,310,546, Gander discloses the use of N-(4-acyloxyphenyl)-all-transretinamide in the prevention of epithelial cancer. The Gander et al. patents, U.S. Pat. Nos. 4,126,693 and 4,190,594, relate to other properties of esters and amides of retinoic acids.

Furthermore, Blazsek et al., *Biomed. Pharmacother.* 45:169–177 (1991), Degos, *Biomed. Pharmacother.* 46:201–209 (1992), Castaigne et al., *Blood* 76 (9):1704–1709 (1990), Chomienne et al., *Blood* 76 (9):1710–1717 (1990), and Lo Coco et al., *Blood* 77 (8):1657–1659 (1991) all disclose using retinoic acid in differentiation therapy for patients with acute promyelocytic leukemia (APL).

Some flavonoids and chalcones have been found to have anti-tumor properties. Middleton et al., *Biochem. Pharmacol.* 43:1167–1179 (1992), relates to the anti-tumor effects of flavonoids, and Harvey et al., *J. Org. Chem.* 53:3936–3943 (1988) and *J. Org. Chem.* 55:6161–6166(1990), and Nair et al., *Carcinogenesis* 12(1):65–69(1991) relate to anti-carcinogenic coumarin and flavone compounds. Jing et al., *Chinese J. Pharmacol. Toxicol.* 6 (4):278–280 (1992) discloses that an isoflavone, diadzein, inhibits melanoma cell growth. The Ishizuka et al. patent, U.S. Pat. No. 5,096,924, discloses anti-cancer effects of a substituted 2-benzopyrinone. Ito et al., U.S. Pat. No. 4,960,908, Briet et al., U.S. Pat. Nos. 4,602,034, 4,783,533, and 5,116,954, and Kramer et al., U.S. Pat. No. 4,713,465, all teach 4-benzopyrinone compounds as anti-cancer agents.

Preuss-Ueberschar et al., *Drug Res.* 34:1305–1313 (1984) discloses that benzopyrones, which include coumarin, are not teratogenic. The pharmacology of coumarin-related compounds is reviewed by Egan et al. which indicates that coumarin-related compounds are known to inhibit the carcinogenicity of carcinogens and that coumarin has been tested for treatment of melanoma.

Edwards et al., *J. Med. Chem.* 33:1948–1954 (1990) relates to the anti-mitotic action of chalcones. Cassady et al. and Ito et al., *Abstract Collection of International Symposium on Recent Advance in Chemistry and Molecular Biology of Cancer Research*, Beijing, China, 1991, pp. 5–6 and 68–69, respectively, relate to the anti-mitogenic effects of various flavonoids, including biochanin A.

Han et al., *Chinese J. Cancer Res.* 2 (3):51–53 (1990), reports the effects of an isoflavone, S86019, which is an active component of a medicinal herb used in China, *Pueraria lobata*. The structure of S86019 is not disclosed. In a different publication, in vivo 4:153–160 (1990), Han et al.

evaluates the $R_{II}$ retinamide compound as a cancer prevention agent and as a cancer chemotherapeutic agent and discusses the induction of cell differentiation of HL60 cells using a combination treatment of $R_{II}$ with S86019. The combination of $R_{II}$ with S86019 acts synergistically in inducing cell differentiation and it is reported that this combination may have clinical applications with minimal patient toxicity.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to overcome one or more deficiencies of the related art, in particular, to overcome the teratogenicity associated with retinoids.

Another object of the present invention is to provide novel retinoids, as coumarin retinoids, and purine retinoids, which have anti-neoplastic activity in vitro.

A further object of the present invention is to provide novel retinoids, as coumarin retinoids, or purine retinoids, which have anti-neoplastic activity in vivo.

A still further object of the present invention is to provide novel retinoid compounds and compositions, using methods of the present invention, which compounds and/or compositions are useful for research and/or pharmaceutical applications in mammals, particularly humans.

The presently claimed retinoid compounds and compositions synergistically combine the cell differentiation activity of retinoids with the anti-carcinogenic properties of coumarins.

One utility of the present invention is the use of such retinoids as a comparative compound or composition for in vitro testing of other compounds for anti-neoplastic activity. Such retinoids are also useful as chemotherapeutic agents in vitro, in situ and/or in vivo.

Yet another object of the present invention is to provide synthetic methods for obtaining retinoid compounds and/or compositions according to formula (I) or (II), as descriptively enabled herein.

Furthermore, the invention is also directed to a method for treating a subject having a precancer or a cancer-related pathology by administering at least one retinoid compound and/or composition comprising or consisting essentially of a coumarin retinoid and/or a purine retinoid, optionally further comprising or consisting essentially of at least one anti-cancer pharmaceutical and/or immunomodulator.

Other features, advantages, embodiments, aspects and objects of the present invention will be clear to those skilled in the areas of relevant art, based on the description, teaching and guidance presented herein.

DETAILED DESCRIPTION OF PREFERRED EMBODIMENTS

Figure 1:
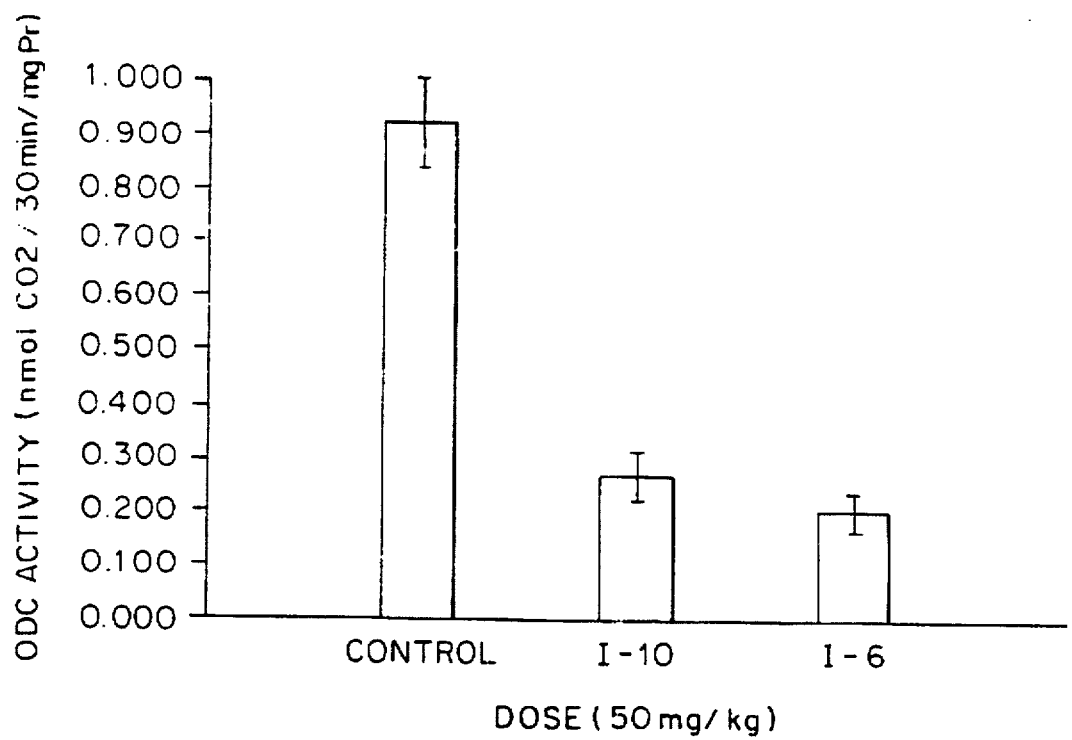
FIG. 1 shows the inhibitory effects of retinoids on croton oil induced ODC activity in mouse epidermis (x±SD, n=3).

The present invention provides a new and biologically active group of retinoids which display cancer chemoprevention activity. These derivatives include, but are not limited to, compounds according to the following formula (I) as coumarin retinoids or formula (II) as purine retinoids.

The coumarin-retinoids in accordance with the present invention have the following formula (I):

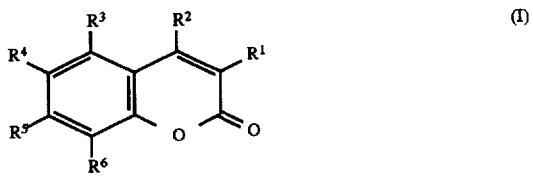

wherein $R^1$=H, $C_1$–$C_{18}$ alkyl, or $COR^7$, where $R^7$=H, OH, $C_1$–$C_{18}$ alkoxy (preferably $C_1$–$C_2$ alkoxy), or $NHR^8$, where $R^8$=H, $C_1$–$C_{18}$ alkyl (preferably $C_1$–$C_2$ alkyl), or unsubstituted or substituted (in which the substituents are preferably selected from OH, COOH, $OCH_3$, and $NO_2$) phenyl; $R^2$ is H, OH, $C_1$–$C_{18}$ alkyl (preferably methyl) or OR, where R=retinoyl; $R^3$ is H, $CH_3$, $COR^7$, OR, or $CH_2OR$, where R and $R^7$ are as defined above; $R^4$ is H, halogen (preferably Cl), $C_1$–$C_{18}$ alkyl, OH, OR, or $COR^7$, where R and $R^7$ are as defined above; $R^5$ is H, $CH_3$ or OR, where R is as defined above; and $R^6$ is H, $CH_3$, OR or $COR^7$, where R and $R^7$ are as defined above; and in which at least one of $R^2$–$R^6$ contains a retinoyl group.

The following compounds (I-1)–(I-38) shown in Table 1 are non-limiting examples of compounds in accordance with the present invention according to Formula I where R=retinoyl:

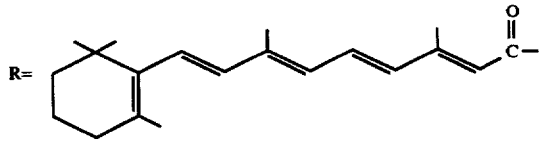

TABLE 1

| Compound | R¹ | R² | R³ | R⁴ | R⁵ | R⁶ |
|---|---|---|---|---|---|---|
| I-1 SLM9133 | COCH₃ | H | H | H | OR | H |
| I-2 XSP4-26 | COCH₃ | H | CH₃ | H | OR | H |
| I-3 XSP4-15A | COCH₃ | H | H | H | OR | CH₃ |

TABLE 1-continued

| Compound | $R^1$ | $R^2$ | $R^3$ | $R^4$ | $R^5$ | $R^6$ |
|---|---|---|---|---|---|---|
| I-4 XSP4-12B | $COCH_3$ | H | $CO_2H$ | H | OR | H |
| I-5 XSP5-5B | $COCH_3$ | H | H | H | OR | $CO_2H$ |
| I-6 XSP4-13A | $COCH_3$ | H | H | Cl | OR | H |
| I-7 XSP4-21 | $COCH_3$ | H | $CH_2OR$ | H | OR | H |
| I-8 XSP5-4A | $COCH_3$ | H | OR | $CO_2H$ | H | H |
| I-9 XSP5-4B | $COCH_3$ | H | H | H | OR | OR |
| I-10 SLM9123 | $COCH_3$ | H | OR | H | OR | H |
| I-11 XSP4-22 | $COCH_3$ | H | $CO_2C_2H_5$ | H | OR | H |
| I-12 SLM9134 | $CO_2C_2H_5$ | H | $CO_2C_{12}H_{25}$ | H | OR | OR |
| I-13 XSP5-14B | $COCH_3$ | H | H | $C_2H_5$ | OR | H |
| I-14 XSP5-15A | $COCH_3$ | H | H | $C_6H_{13}$ | OR | $CH_3$ |
| I-15 SLM92-2 | $CO_2C_2H_5$ | H | H | H | OR | $CH_3$ |
| I-16 SLM$_{III}$ | $COCH_3$ | H | H | $COCH_3$ | OR | H |
| I-17 XSP5-14A | $CO_2C_2H_5$ | H | H | H | OR | H |
| I-18 XSP4-30 | $CO_2C_2H_5$ | H | H | Cl | OR | H |
| I-19 XSP4-25 | $CO_2C_2H_5$ | H | $CO_2H$ | H | OR | H |
| I-20 SLM9126 | $CO_2C_2H_5$ | H | H | H | OR | OR |
| I-21 SLM9147 | $CO_2C_2H_5$ | H | OR | H | OR | H |
| I-22 SLM$_{III}$-13 | $CO_2C_2H_5$ | H | H | $C_2H_5$ | OR | H |
| I-23 XSP5-12B | $CO_2C_2H_5$ | H | H | H | OR | $COCH_3$ |
| I-24 SLM$_{II}$-20 | $CO_2C_2H_5$ | H | OR | $COC_6H_5$ | H | H |
| I-25 SLM$_{III}$-12 | $CO_2H$ | H | H | $C_6H_{13}$ | OR | H |
| I-26 XSP5-5A | $CONH_2$ | H | $CO_2H$ | H | OR | H |
| I-27 XSP5-3B | $CONH_2$ | H | H | Cl | OR | H |
| I-28 XSP5-29B | H | OR | H | t-Bu | H | H |
| I-29 XSP-30A | H | OR | H | H | H | $CH_3$ |
| I-30 XSP-30B | H | $CH_3$ | H | H | OR | $CH_3$ |
| I-31 S2-01B | H | $CH_3$ | H | $C_2H_5$ | OR | H |
| I-32 S41 | H | $CH_3$ | H | H | OR | H |
| I-33 S42 | H | $CH_3$ | OR | H | OR | H |
| I-34 S44 | H | $CH_3$ | H | $C_6H_{13}$ | OR | H |
| I-35 S46A | H | OR | H | $CH_3$ | H | H |
| I-36 546B | H | $CH_3$ | H | H | OR | OR |
| I-37 | H | OR | H | H | $CH_3$ | H |
| I-38 | H | OR | H | H | H | H |

The purine retinoids in accordance with the present invention have the following formula (II):

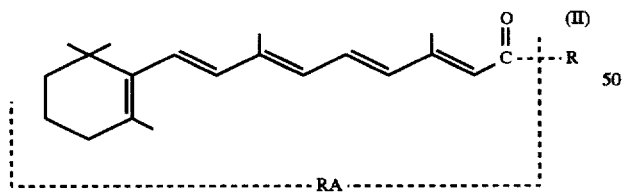

wherein R=

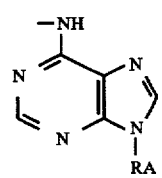

II-A

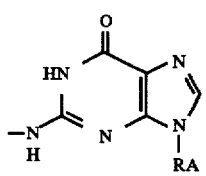

II-B

II-C

II-D

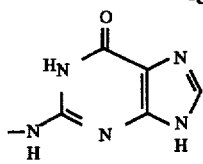

II-E

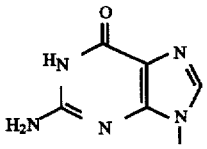

II-F

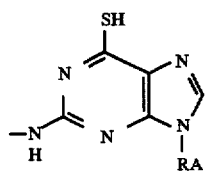

II-G

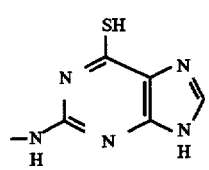

II-H

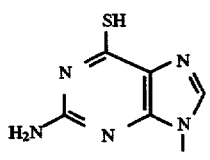

II-I

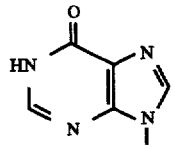

II-J

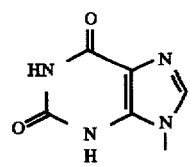

II-K

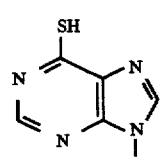

II-L

The foregoing compounds (II-A)–(II-L) provide non-limiting examples of compounds according to formula (II). Such compounds, or isomers thereof, in any combination are provided as compounds or compositions according to the present invention.

Such retinoids of the present invention are unexpectedly discovered to have anti-cancer activity, thus providing suitable compounds and compositions for treatment of cancer-related pathologies, optionally with additional pharmaceutically active ingredients, such as antiviral, chemotherapeutic agents and/or immuno-stimulating compounds, or antiviral antibodies or fragments thereof, in vitro, in situ, and/or in vivo.

Cancer-related pathologies in the context of the present invention include, but are not limited to, tumors and pathologies involving tumorigenesis, leukemias, lymphomas, melanomas, sarcomas, virus-related cancers, and any other known cancers.

The term "anti-cancer activity" is intended to mean the ability to induce at least one of (1) inhibition of growth or mitosis of transformed, mutated, preneoplastic or neoplastic cells; (2) promotion of apoptosis; and/or (3) angiogenesis inhibition.

In the context of the present invention, the term inhibition or stimulation, as a quantitative value, is between 10 and 100 percent inhibition and 10 and 1000 percent stimulation, relative to a suitable control, such as, but not limited to the same cell or animal under the same conditions, except for the presence or administration of one or more retinoids according to the present invention.

The present invention also provides synthetic methods for obtaining retinoid compounds according to formula (I) or formula (II), which would be clear to one of ordinary skill in the art, based on the teaching and guidance presented herein, in combination with what is known in the related fields of art. In general, components of completely synthesized coumarin or purine compounds and/or retinoyl compounds can be provided as starting materials, and the appropriate side groups can be added, modified or used in suitable, known chemical reaction steps to provide retinoid compounds according to formula (I) or formula (II).

Testing Anti-Cancer Activity

There are many known in vitro assays for determining whether a given compound and/or composition has anti-neoplastic activity. Such methods are well known in the art and provide the means for one of ordinary skill in the art to determine, using routine experimentation, whether a given retinoid of the present invention has a specific anti-cancer activity for a given cancer-related pathology.

The following are examples of methods which can be used to screen coumarin retinoids and purine retinoids according to formula (I) or formula (II) for determining at least one pharmaceutical utility; without undue experimentation, based on the teaching and guidance presented herein.

Non-limiting examples of anti-neoplastic in vitro activity, include but are not limited to, activity (1) against phosphorylation of phospholipids promoted by tetradecanoylphorbol-13-acetate in HeLa cells as a screening test for anti-tumor promoting effect; (see, e.g., Shibata, *Stem Cells* 12:44–52 (1994)); (2) soft agar clonogenic assays (e.g., Rangel et al., *Cancer Chemother. Pharmacol.* 33:460–64 (1994)); (3) cytostatic activity in cancer cells (see, e.g., Rajala et al., *Ann. Chir. Gynacol. Suppl.* 206:50–53 (1993)); inhibition of proliferation of human gastric cancer derived cells (Shibata, supra); (3) cytotoxic activity against cancer cell systems (see, e.g., Ngassapa et al., *J. Nat. Prod.* 56:1676–81 (1993); Sanyal et al., *Neoplasma* 40:219–22 (1993); Perez et al., *Cancer Chemother. Pharmacol.* 33:245–250 (1993)); Hahn et al., *Cancer* 72:2705–11 (1993)); (4) inhibition of tumor colony forming units (see, e.g., Eckardt et al., *J. Nat'l Cancer Inst.* 86:30–33 (1994); Chen et al., *Anticancer Drugs* 4:447–57 (1993)); (5) cell differentiation of human promyelocytic leukemia cells; and (6) MTT assay for inhibition of cancer cells, the contents of which references are entirely incorporated herein by reference.

Non-limiting examples of anti-neoplastic in vivo activity include, but are not limited to, activity in (1) inhibition of tumorigenesis in mouse skin tumors (see, e.g., Shibata, *Stem Cells* 12:44-52 (1994)); (2) inhibition of animal carcinogenesis model systems (see, e.g., Kennedy, *Prev. Med.* 22:796-811 (1993); Johnson et al., *Cancer Chemother. Pharmacol.* 32:339-46 (1993)), such as nude mice or chimeric nude mice (see, e.g., Toppet al., *Blood* 82:2837-44 (1993); Sailkawa et al., *Jpn. J. Cancer Res.* 84:787-93 (1993)); (3) monocyte activation assay (Shi et al., *Cancer Res* 53:3986-91 (1993)); (4) serum tumor necrosis activity assay (Shi et al., *Cancer Res* 53:3986-91 (1993)); (5) croton oil induced ear edema in mice; and (6) croton oil induced ODC activity in mouse epidermis; the contents of which references are entirely incorporated herein by reference.

Additionally, predictive statistics and artificial intelligence can be used to provide computer programs which integrate matrix data to calculate patterns of activity, structural motifs, and a cell's expression of molecular targets to predict a given compound's mechanism of action to combine screening assay data and structure based drug design and testing. Weinstein et al., *Stem Cells* 12:12-22 (1994), the contents of which reference is entirely incorporated herein by reference.

Pharmaceutical Compositions Pharmaceutical compositions comprising coumarin retinoid compounds and/or purine retinoid compounds of the present invention, include all compositions wherein at least one pharmaceutical compound or composition is contained in an amount effective to achieve its intended purpose. In addition, pharmaceutical compositions containing at least one pharmaceutical compound or composition may contain suitable pharmaceutically acceptable carriers comprising excipients and auxiliaries which facilitate processing of the active compounds into preparations which can be used pharmaceutically. Pharmaceutical compositions of the present invention can also include anti-neoplastics and/or immunomodulators.

A pharmaceutical compound or composition of the present invention may further comprise or consist essentially of at least one member selected from a single chain ribosome inhibitory protein (acting to block expression of a cancer related protein in a cancer related receptor cell or tissue); a cytokine; or a growth factor.

Cytokines that are produced by lymphocytes are termed lymphokines, whereas peptides produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells. Cytokines used according to the present invention are those suitable for use as additional active ingredients of compositions of the present invention.

According to another aspect of the present invention, a cytotoxic or a chemotherapeutic agent may be further included in a pharmaceutical composition of the present invention, optionally further comprising a delivery vector that preferentially binds to, or facilitates association of the pharmaceutical/diagnostic compound or composition with pathologic cells as target cells involved in cancer. The targets for this type of therapy can also be growth factor receptors, differentiation antigens, or other less characterized cell surface antigens specifically associated with cancer or precancer cells.

Pharmaceutical compositions can also include suitable solutions for administration by injection or orally, and contain from about 0.001 to 99 percent, preferably from about 20 to 75 percent of active component. Pharmaceutical compositions for oral administration include tablets and capsules. Compositions which can be administered rectally include suppositories.

Pharmaceutical carriers for the active ingredient may be either in sprayable or nonsprayable form. Non-sprayable forms can be semi-solid or solid forms comprising a carrier conducive to topical application and having a dynamic viscosity preferably greater than that of water. Also suitable for systemic or topical application, in particular to the mucous membranes and lungs, are sprayable aerosol preparations where the active ingredient is preferably in combination with a solid or liquid inert carrier material. The aerosol preparations can contain solvents, buffers, surfactants, perfumes, and/or antioxidants in addition to the retinoid compounds or compositions of the present invention.

Pharmaceutical Administration. Pharmaceutical administration of a pharmaceutical compound or composition of the present invention may be administered by any means that achieve its intended purpose, for example, to treat or prevent a cancer or precancerous condition.

The term "protection", as in "protection from a cancerous or precancerous condition", as used herein, encompasses "prevention," "suppression" or "treatment." "Prevention" involves administration of a pharmaceutical composition prior to the induction of the disease. "Suppression" involves administration of the composition prior to the clinical appearance of the disease. "Treatment" involves administration of the protective composition after the appearance of the disease. It will be understood that in human and veterinary medicine, it is not always possible to distinguish between "preventing" and "suppressing" since the ultimate inductive event or events may be unknown, latent, or not ascertained in the patient until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." See, e.g., Berkow et al. eds., *The Merck Manual*, 16th edition, Merck and Co., Rahway, N.J., 1992; Goodman et al., eds., Goodman and Gilman's *The Pharmacological Basis of Therapeutics*, 8th edition, Pergamon Press, Inc., Elmsford, N.Y., (1990); Katzung, *Basic and Clinical Pharmacology*, Appleton and Lange, Norwalk, Conn., (1992), which are entirely incorporated herein by reference, including all references cited therein. The "protection" provided need not be absolute, i.e., the disease need not be totally prevented or eradicated, provided that there is a statistically significant improvement (p=0.05) relative to a control population. Protection may be limited to mitigating the severity or rapidity of onset of symptoms of the disease.

At least one retinoid compound or composition of the present invention may be administered by any means that achieves the intended purpose, using a pharmaceutical composition as previously described.

For example, administration may be by various parenteral routes such as subcutaneous, intravenous, intradermal, intramuscular, intraperitoneal, intranasal, intracranial, transdermal, or buccal routes. Parenteral administration can also be by bolus injection or by gradual perfusion over time. Alternatively, or concurrently, administration may be by the oral route.

An additional mode of using of a pharmaceutical compound or composition of the present invention is by topical application. A pharmaceutical compound or composition of the present invention may be incorporated into topically applied vehicles such as salves or ointments.

A typical regimen for treatment or prophylaxis includes administration of an effective amount over a period of one or several days, up to and including between one week and about six months.

It is understood that the dosage of a pharmaceutical compound or composition of the present invention administered in vivo will be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage will be tailored to the individual subject, as is understood and determinable by one skilled in the relevant arts. See, e.g., Berkow et al, supra, Goodman et al, supra, and Katzung, supra; *Avery's Drug Treatment: Principles and Practice of Clinical Pharmacology and Therapeutics*, 3rd edition, ADIS Press, LTD., Williams and Wilkins, Baltimore, Md. (1987), Ebadi, Pharmacology, Little, Brown and Co., Boston, (1985), which references are entirely incorporated herein by reference.

The total dose required for each treatment may be administered by multiple doses or in a single dose. The pharmaceutical compound or composition may be administered alone or in conjunction with other pharmaceuticals directed to the pathology, or directed to other symptoms of the pathology.

Effective amounts of a pharmaceutical compound or composition of the present invention are from about 0.001 µg to about 100 mg/kg body weight, preferably about 5 mg/kg to 100 mg/kg body weight, most preferably about 20 mg/kg to 50 mg/kg body weight administered at intervals of 4–72 hours, for a period of 2 days to 5 years.

The compounds and/or compositions of the present invention are to be administered to preferably mammalian recipients, most preferably humans.

Having now generally described the invention, the same will be more readily understood through reference to the following example which is provided by way of illustration, and is not intended to be limiting of the present invention.

EXAMPLE 1

A Coumarin Retinoid Compound According to Formula I

Preparation of 3-acetyl-5-carboxy-7-retinoyloxy coumarin (I-4)

A 100 ml round-bottomed flask was fitted with a magnetic stirrer and a condenser, the upper end of which was protected by a calcium chloride tube. In the flask, a mixture of 0.6 g (0.002M) of retinoic acid, 20 ml of benzene and 0.12 ml (0.0013M) of $PCl_3$ was stirred for 1 hr at room temperature under $N_2$. The reaction mixture was then concentrated with a rotavapor, and the residue was dissolved in 20 ml of absolute ether. This absolute ether solution was added dropwise at room temperature with stirring into a mixture of 0.5 g (0.002M) of 3-acetyl-5-carboxy-7-hydroxycoumarin, 0.5 ml of pyridine and 20 ml absolute ether in a 100 ml, three necked, round-bottomed flask. After stirring for another two hrs., the solid produced was collected by filtration, then dried and crystallized with ethanol. 0.7 g of the pure product was obtained with the following characteristics: mp: 145°–47° C., NMR $CDCl_3$ δ 1.03(s, 6H, 1'-bis-$CH_3$); 1.38–2.14 (m, 6H, aliphatic cycle-$CH_2$—); 1.71(s,3H,5'-$CH_3$); 2.02(s, 3H, 9'-$CH_3$); 2.42(s, 3H, 13'-$CH_3$); 2.70(s, 3H, 3-$COCH_3$); 4.76(b, 1H, 5-$CO_2$H); 5.93–6.41 and 6.97–7.26, (m, 6H, double bond hydrogen of retinoyl); 7.40 (d, 1H, 8-H); 7.85(d, 1H, 6-H); 9.51 (s, 1H, 4-H); MS $C_{32}H_{34}O_7$= 530 ($M^+$), 282 (retinoyl), 248 (coumarin), 233 (100, 248-$CH_3$).

EXAMPLE 2

A Coumarin Retinoid Compound According to Formula I

Preparation of 3-acetyl-5-ethoxycarbyl-7-retinoyloxy-coumarin (I-11) is under the same conditions as in Example 1 where 0.5 g of the product was obtained from 0.56 g (0.002M) of 3-acetyl-5-ethoxycarboxy-7-coumarin and 0.6 g (0.002M) of retinoic acid (purified with ethanol), having mp: 162°–64° C.; NMR $CDCl_3$ δ 1.04(s, 6H-1'-bis-$CH_3$); 1.44(t, 3H, 5-ester-$CH_3$); 1.14–2.12(m, 6H, aliphatic cycle $CH_2$—); 1.72(s, 3H, 5'-$CH_3$); 2.03(s, 3H, 9'-$CH_3$); 2.42(s, 3H, 13'-$CH_3$); 2.70(s, 3H, 3-$COCH_3$); 4.24(q, 2H, 5-ester-$CH_2$); 5.88–6.48 and 6.98–7.25 (m, 6H, double bond hydrogen of retinoyl; 7.36 (d, 1H, 8-H); 7.73(d, 1H, 6-H); 9.47 (s, 1H, 4-H); MS $C_{34}H_{38}O_7$=558 ($M^+$, nearly basic peak) 283, 276, 261, 233, 231, 175 (100, 231-28-28).

EXAMPLE 3

A Coumarin Retinoid Compound According to Formula I

Preparation of 4-retinoyloxy-6-t-butyl-coumarin (I-28) is under the same conditions as in Example 1 where 0.6 g of product was obtained (yield 43%) from 0.6 g of 4-hydroxy-6-t-butly-coumarin and 1.0 g of retinoic acid, mp: 142°–44° C. $^1HNMR$ δ ($CDCl_3$) 1.05(s, 6H, 1'-2$CH_3$), 1.37(s, 9H, t-But-3$CH_3$), 1.48, 1.62 and 2.04(m, 6H, cycle-CH), 1.73(s, 3H, 5'-$CH_3$), 2.05(s, 3H, 9'-$CH_3$), 2.46(s, 3H, 13'-$CH_3$), 6.06(s, 1H, 3-H), 6.16–6.52 and 7.16–7.26(m, 6H, alkene-H), 7.30(d, 1H, Ar—H), 7.61(m, 2H, Ar—H). MS:500($M^+$), 282, 218, 203, 175, 161.

EXAMPLE 4

A Coumarin Retinoid Compound According to Formula I

Preparation of 4-retinoyloxy-7-methyl-coumarin (I-37) is under the same conditions as in Example 1 where 0.5 g of product was obtained (yield 50%) from 0.4 g of 4-hydroxy-7-methyl-coumarin and 1.0 g of retinoic acid, 115°–117° C., $^1HNMR$ δ ($CDC_3$) 1.03(s, 6H, 1'-2$CH_3$), 1.32–2.14(m, 6H, cycle-$CH_2$), 1.71(s, 3H, 5'-$CH_3$), 2.30(s, 3H, 9'-$CH_3$), 2.42 (s, 6H, 7, 13'-2$CH_3$), 5.92(s, 1H, 3-H), 5.96–6.50 and 6.92–7.26(m, 6H, alkene-H), 7.10(m, 2H, Ar—H), 7.48(d, 1H, Ar—H). MS: 458($M^+$), 430, 355, 321, 307, 282, 267, 175, 159, 147.

EXAMPLE 5

A Coumarin Retinoid Compound According to Formula I

Preparation of 4-methyl-7-retinoyloxy-coumarin (I-32) is under the same conditions as in Example 1 where 0.54 g of product was obtained (yield 39%) from 0.57 g of 4-methyl-7-hydroxy-coumarin and 1.0 g of retinoic acid, mp: 178°–80° C., $^1HNMR$ ε ($CDCl_3$), 1.04(s, 6H, 1'-2$CH_3$), 1.16–2.28(m, 6H, cycle-$CH_2$), 1.73(s, 3H, 5'-$CH_3$), 2.01(s, 3H, 9'-$CH_3$), 2.28(s, 3H, 13'-$CH_3$), 2.41(s, 6H, 4, 8-2$CH_3$), 5.99(s, 1H, 3-H), 6.01–6.56 and 6.86–7.28(m, 6H, alkene-H), 7.06(d, 1H, ArH), 7.40(d, 1H, Ar—H).

MS: 472($M^+$), 283, 190, 175, 161.

EXAMPLE 6

A Coumarin Retinoid Compound According to Formula I

Preparation of 4-methyl-6-ethyl-7-retinoyloxy-coumarin (I-31) is under the same conditions as in Example 1 where 0.43 g of product was obtained (yield 43%) from 0.61 g of 4-methyl-6-ethyl-7-hydroxy-coumarin and 1.0 g of retinoic acid, mp: 120°–2° C., $^1HMR$ δ ($CDCl_3$), 1.05(s, 6H, 1'-2$CH_3$), 1.22(t, 3H, 6-Et-$CH_3$), 1.16–2.24(m, 6H, cycle-$CH_2$) 1.72(s, 3H, 5'-$CH_3$), 2.02(s, 3H, 9'-$CH_3$), 2.41(s, 3H, 13'-$CH_3$), 2.66(q, 2H, 6-Et-$CH_2$), 6.00(s, 1H, 3-H), 6.06–6.50 and 6.88–7.26(m, 6H, alkene-H), 7.07(s, 1H, Ar—H), 7.41(s, 1H, Ar—H). MS: 486(M⁺), 470, 363, 283, 204, 189, 175, 161.

EXAMPLE 7

A Coumarin Retinoid Compound According to Formula I

Preparation of 4-methyl-7-retinoyloxy-coumarin is under the same conditions as in Example 1 where 0.64 g was obtained (yield 61.5%) from 0.4 g of methyl-7-hydroxy-coumarin and 0.9 g of retinoic acid, mp: 154°–6° C., ¹HMR, δ (CDCl₃): 1.04(s, 6H, 1'-2CH₃), 1.47, 1.62 and 1.94(m, 6H, cycle-CH₂), 1.72(s, 3H, 5'-CH₃), 2.03(s, 3H, 9'-CH₃), 2.42–2.44(d, 6H, 4, 13'-2CH₃), 5.98(s, 1H, 3-H), 6.15–6.39 and 7.09–7.12(m, 6H, alkene-H), 7.15(m, 2H, Ar—H), 7.60(d, 1H, Ar—H). MS: 458(M⁺), 283, 175, 161, 148.

EXAMPLE 8

A Coumarin Retinoid Compound According to Formula I

Preparation of 4-methyl-5,7-diretinoyloxy-coumarin (I-33) is under the same conditions as in Example 1 where 0.75 g was obtained (yield 36.6%) from 0.52 g of 4-methyl 5,7-dihydroxy-coumarin and 2 g of retinoic acid, mp: 134°–36° C., ¹HMR, δ (CDCl₃): 1.04(s, 12H, 1', 1"-4CH₃), 1.48, 1.62 and 2.00[m, 12H, bis-(cycle-CH₂)], 1.73(S, 6H, 5', 5"-2CH₃), 2.04(6H, 9', 9"-2CH₃), 2.48(d, 6H, 13', 13"-2CH₃), 2.63(S, 3H, 4-CH₃), 5.97(s, 1H, 3-H), 6.15–6.40 and 6.93–7.17(m, 12H, alkene-H, 7.13(d, 1H, Ar—H), 7.16(d, 1H, Ar—H). MS: 474(M⁺–282), 283, 192, 175, 161.

EXAMPLE 9

A Coumarin Retinoid Compound According to Formula I

Preparation of 4-methyl-6-hexyl-7-retinoyloxy-coumarin (I-34) is under the same conditions as in Example 1 where 1.0 g was obtained (yield 41.0%) from 0.7 g of 4-methyl-6-hexyl-7-hydroxy-coumarin and 1.0 g of retinoic acid, mp: 114°–5° C. ¹HMR, (CDCl₃): 0.87(t, 3H,6-hex-CH₃), 1.04(s, 6H, 1'-2CH₃)1.02–2.63(m, 14H, 6-hex-and cycle-CH₂)1.73 (s, 3H, 5'-CH₃), 2.03(s, 3H, 9'-CH₃), 2.42(s, 6H, 4, 13'-2CH₃), 2.58(m, 2H, 6-hex-CH₂), 6.02(s, 1H, 3-H), 6.16–6.41 and 7.06–7.40(m, 6H, alkene-H), 7.10(s, 1H, Ar—H), 7.42(s, 1H, Ar—H). MS: 542(M⁺), 527, 283, 260, 189, 175, 161, 135.

EXAMPLE 10

A Coumarin Retinoid Compound According to Formula I

Preparation of 4-retinoyloxy-6-methyl-coumarin (I-35) is under the same conditions as in Example 1 where 0.73 g was obtained (yield 56.3%) from 0.5 g of 4-hydroxy-6-methyl-coumarin and 1.0 g of retinoic acid, mp: 104°–6° C., ¹HMR, δ (CDCl₃), 1.04(s, H, 1'-2CH₃), 1.42, 1.62 and 2.03(m, 6H, cycle-CH₂), 1.73(s, 3H, 5'-CH₃) 2.04(s, 3H, 9'-CH₃), 2.43(d, 6H, 6, 13'-2CH₃), 6.05(s, 1H, 3-H), 6.17–6.50 and 7.16(m, 6H, alkene-H), 7.25(m, 2H, Ar—H, 7.37(d, 1H, Ar—H). MS: 458(M⁺), 444, 430, 282, 176, 161.

EXAMPLE 11

A Coumarin Retinoid Compound According to Formula I

Preparation of 4-methyl-7,8-diretinoyloxy-coumarin (I-36) is under the same conditions as in Example 1 where 1.65 g was obtained (yield 73.5%) from 0.57 g of 4-Methyl-7,8-dihydroxy-coumarin and 1 g of retinoic acid, mp: 106°–8° C. ¹HNMR, δ (CDCl₃), 1.03(s, 12H, 1', 1"-4CH₃), 1.10–2.61(m, 12H, cycle-CH₂) 1.66 (s, 6H, 5',5"-2CH₃), 2.00(s, 6H, 9",9'-2CH₃), 2.17(s, 6H, 13", 13'-2CH₃), 2.24(s, 3H, 4-CH₃), 5.92(s, 1H, 3-H), H), 6.04–6.91 and 6.84–7.14 (m, 12H, alkene-H), 7.18(d, 1H, Ar—H), 7.44(d, 1H, Ar—H). MS: 474(M⁻282), 283, 192, 175, 161.

EXAMPLE 12

A Coumarin Retinoid Compound According to Formula I

Preparation of 4-retinoyloxy-coumarin (I-38) is under the same conditions as in Example 1 where 0.65 g was obtained (yield 30%) from 0.8 g of 4-hydroxy-coumarin and 2.0 g of retinoic acid. mp: 88°–91° C. ¹HNMR δ (CDCl₃), 1.04(s, 6H, 1'-CH₃), 1.48–2.62(m, 6H, cycle-CH₂), 1.64(s, 3H, 5'-CH₃), 2.04(s, 3H, 9'-CH₃), 2.36(s, 3H, 13'-CH₃), 6.03(s, 1H, 3-H), 6.13–6.5 and 7.01–7.21(m, 6H, alkene-H), 7.27–7.69(m, 4H, Ar—H). MS: 444(M⁺), 429, 416, 282, 255, 175, 161, 159, 135.

EXAMPLE 13

Preparation of a purine retinoid according to formula (II)

For the preparation of the desired compounds, all-trans-retinoic acid (0.01M) and phosphorus trichloride (0.003 M) were combined in a round bottom flask and 60 ml petroleum ether was added and stirred. The reaction mixture in the flask was heated and refluxed. At this step, hydrogen chloride was produced and allowed to escape with the reaction solution turning to be brown-yellowish transparent solution. The reaction solution was decanted and distilled to remove the solvent and the residue was then dissolved with acetate ether.

Compounds with an amino or hydroxy group (0.01M) was dissolved in an appropriate solvent at room temperature and the prepared retinoyl chloride was added dropwise. The resultant precipitate was formed instantly and the color of reaction solution deepened. The reaction was allowed to continue for two hours or overnight at room temperature. The reactant was filtered and the resultant product was washed or recrystallized. The filtrate was concentrated and recrystallized or chromatographed for purification. The product was checked by thin layer chromatography and the melting point of the compound was also studied. The parameters for structure identification of purine retinoid II-A were as follows:

UV: $\lambda_{max}$-EtOH 340 nm E=5180

IR: KBr cm⁻ 1690 —CONHR, 1670 —CON<

MS: m/2 700 M⁺, 699 (M–1)

HNMR: CDC13 δppm 1.05 (12H, S, CH₃) 1.5~1.7 (8H, m, CH₂) 1.75 (6H, S, CH₂) 2.05 (6H, S, CH₃) 2.55 (6H, S, CH₃) 2.05 (4H, t, CH₂)

Element Analysis: calculated value: C 75.28, H 8.28, N 9.75 determined value: C 75.27, H 8.55, N 9.33

EXAMPLE 14

Cell Differentiation Activity of Coumarin-Retinoids

Human promyelocytic leukemia HL-60 cells were cultured in RPMI-1640 medium supplemented by 10% heat-inactivated calf serum and 100 U/ml of penicillin plus 100 μg/ml of streptomycin. The flasks containing cells and medium were incubated in an incubator with 5% $CO_2$ at 37° C. Log phase cells were seeded into the medium at a concentration of $1.2\times10^5$ to $1.4\times10^5$ cells per ml and cultured in flasks containing 5 ml of medium. Each group consisted of three flasks. Different concentrations of coumarin-retinoids were added. At intervals following the addition of coumarin-retinoids to the cultures, a small portion of cells was removed and live cells were counted under a light microscope using a dye-exclusion method with trypan blue. Cell differentiation was judged in terms of morphology and nitroblue tetrazolium (NBT) reduction.

For a determination of NBT reducing activity, a portion of the coumarin-retinoid-treated cells was removed at intervals following treatment and centrifuged. After centrifugation, 0.5 ml of 0.1% NBT (containing 100 ng TPA) was added to each tube. The contents of the test tubes were then incubated for 1 hour at 37° C. Cell smears were prepared from the cell sediment and stained using the Wright-Giemsa technique. For each smear prepared, 200 cells were isolated for examination under a light microscope with an oil immersion lens. Cells stained with blue-black granules were considered NBT-positive cells. The 50% differentiation or effective concentration ($ED_{50}$ or $EC_{50}$) is shown in terms of molar (M) concentration of the coumarin-retinoid tested.

For a determination of cell morphology, a cell smear was prepared at intervals following treatment of cells for each coumarin-retinoid concentration group using the Wright-Giemsa stain technique. Stained cells were counted and classified under a light microscope with an oil immersion lens. After treatment with coumarin-retinoids, the morphological development of HL-60 cells proceeded toward mature granulocytes. This development was manifested by decreased cell volume; a lower nuclei to cytoplasm ratio; smaller or missing nuclei; concentration of chromatin; and the appearance of a certain proportion of intermediate and late granuloblasts (progranulocytes), elongated rod granulocytes, and granulocytes with branched nuclei.

TABLE 2

| Compound | Concentration (M) | NBT (+) % | $EC_{50}$ (M) |
|---|---|---|---|
| I-11 | $10^{-4}$ | 77 | $3 \times 10^{-6}$ |
| | $10^{-5}$ | 72 | |
| | $10^{-6}$ | 49 | |
| | $10^{-7}$ | 8 | |
| I-19 | $10^{-7}$ | 92 | $9 \times 10^{-6}$ |
| | $10^{-4}$ | 84 | |
| | $10^{-5}$ | 5 | |
| I-2 | $10^{-6}$ | 84 | $2 \times 10^{-6}$ |
| | $10^{-5}$ | 38 | |
| | $10^{-6}$ | 2 | |
| I-12 | $10^{-5}$ | 82 | $1 \times 10^{-8}$ |
| | $10^{-6}$ | 47 | |
| | $10^{-7}$ | 30 | |
| | $10^{-8}$ | 0 | |
| | $10^{-9}$ | 0 | |
| I-10 | $6.4 \times 10^{-6}$ | 99 | $1.3 \times 10^{-8}$ |
| | $6.4 \times 10^{-7}$ | 96 | |
| | $6.4 \times 10^{-8}$ | 82 | |
| | $6.4 \times 10^{-9}$ | 33 | |
| | $6.4 \times 10^{-10}$ | 10 | |
| I-6 | $10^{-4}$ | 96 | $6 \times 10^{-7}$ |
| | $10^{-5}$ | 81 | |
| | $10^{-6}$ | 78 | |
| | $10^{-7}$ | 31 | |
| | $10^{-8}$ | 2 | |
| I-7 | $10^{-5}$ | 85 | $7.5 \times 10^{-7}$ |
| | $10^{-6}$ | 65 | |
| | $10^{-7}$ | 12 | |
| I-27 | $10^{-5}$ | 88 | $5.5 \times 10^{-7}$ |
| | $10^{-6}$ | 80 | |
| | $10^{-7}$ | 17 | |
| I-8 | $10^{-5}$ | 98 | $5.9 \times 10^{-8}$ |
| | $10^{-6}$ | 69 | |
| | $10^{-7}$ | 55 | |
| | $10^{-8}$ | 34 | |
| I-9 | $10^{-5}$ | 96 | $6.5 \times 10^{-8}$ |
| | $10^{-6}$ | 88 | |
| | $10^{-7}$ | 55 | |
| | $10^{-8}$ | 31 | |
| I-15 | $10^{-5}$ | 93 | $2.6 \times 10^{-7}$ |
| | $10^{-6}$ | 84 | |
| | $10^{-7}$ | 46 | |
| | $10^{-8}$ | 12 | |
| I-21 | $10^{-5}$ | 94 | $2.5 \times 10^{-7}$ |

TABLE 2-continued

| Compound | Concentration (M) | NBT (+) % | $EC_{50}$ (M) |
|---|---|---|---|
| | $10^{-6}$ | 80 | |
| | $10^{-7}$ | 41 | |
| | $10^{-8}$ | 17 | |
| I-26 | $10^{-5}$ | 97 | $8.0 \times 10^{-8}$ |
| | $10^{-6}$ | 91 | |
| | $10^{-7}$ | 53 | |
| | $10^{-8}$ | 34 | |
| I-5 | $10^{-5}$ | 89 | $2.8 \times 10^{-7}$ |
| | $10^{-4}$ | 69 | |
| | $10^{-7}$ | 41 | |
| I-4 | $10^{-5}$ | 92 | $7 \times 10^{-8}$ |
| | $10^{-6}$ | 84 | |
| | $10^{-7}$ | 73 | |
| | $10^{-8}$ | 15 | |
| I-18 | $10^{-5}$ | 44 | $1 \times 10^{-5}$ |
| | $10^{-6}$ | 8 | |
| I-17 | $10^{-5}$ | 84 | $1 \times 10^{-6}$ |
| | $10^{-6}$ | 54 | |
| | $10^{-7}$ | 2 | |
| I-3 | $10^{-5}$ | 88 | $8 \times 10^{-7}$ |
| | $10^{-6}$ | 77 | |
| | $10^{-7}$ | 12 | |

EXAMPLE 15

Anti-Teratogenicity Effect of Retinoids on Fetus Absorption in Mice

Female mice were examined by vaginal smear the morning after being caged with male mice, and if sperm or a vaginal plug was discovered, then the mice were determined to be pregnant. The retinoids were administered at the dosage indicated starting on the seventh day of pregnancy and continued once a day for the next ten days. On the 20th day after the female mice were determined to be pregnant, they were sacrificed by cervical dislocation. Both sides of the uterus were checked and the number of living embryos, dead embryos, and absorbed embryos were counted. The living embryos were further examined for bone abnormalities.

TABLE 3

Effect of I-10 on fetus absorption in mice

| Group | Dosage (mg/kg) | Fetus Absorption (%) absorbed number/implanted number |
|---|---|---|
| Control | | 0/135 |
| Tween 80 | 0.3% | 0/104 |
| I-10 | 40 | 0/107 |
| | 20 | 0/104 |
| All Trans RA | 10 | 73/99 (73.7%) |

TABLE 4

Effect of I-9 on fetus absorption in mice

| Group | Dosage (mg/kg) | Fetus Absorption (%) absorbed number/implanted number |
|---|---|---|
| Control | | 0/135 |
| Tween 80 | 0.3% | 0/104 |
| I-9 | 40 | 0/119 |
| | 20 | 0/113 |
| All Trans RA | 10 | 73/99 (73.7%) |

TABLE 5

Effect of II-A on fetus absorption in mice

| Group | Dosage (mg/kg) | Pregnant Mice | Implanted Number | Absorbed Number |
|---|---|---|---|---|
| Control |  | 14 | 153 | 0 |
| II-A | 20 | 12 | 141 | 10 |
|  | 40 | 15 | 181 | 17 |
| Tween 80 | 0.3% | 15 | 184 | 4 |
| All Trans RA | 15 | 15 | 186 | 111 |

EXAMPLE 16

Effect of Coumarin Retinoids on Croton Oil Induced Ornithine Decarboxylase Enzyme Activity in Mouse Epidermis ICR mice (6–8 weeks old) were pretreated with a single dose of coumarin retinoid. On the third day, the animals received a topical application of 0.2 ml of 1% croton oil in acetone. All animals were sacrificed five hours after the croton oil treatment and the epidermis was separated by a brief heat treatment at 52° C. for 30 seconds and minced in a blender. The cell suspension and broth were separated by a centrifugation at 30,000×g for 30 seconds and the supernatant was obtained. Ornithine decarboxylase (ODC) enzyme activity was determined by measuring the release of $CO_2$ from L-($^{14}C$)-ornithine and expressed as nmole $CO_2$/30 min/mg protein and the results for coumarin retinoid I-10 and I-6 are shown in FIG. 1. As can be seen in FIG. 1, the coumarin retinoids significantly inhibited the ODC activity induced by croton oil. ODC activity is a critical parameter for monitoring cancer chemoprevention or promotion.

EXAMPLE 17

Anti-Oxidation Effect of Coumarin Retinoids

Lipid peroxidation was induced by adding 1 mM $FeSO_4$ and 10 mM cysteine to the microsome fraction of rat liver with the incubations being carried out at 37° C. for 30 minutes in a reaction mixture containing 10 mM phosphate buffer (pH 7.4). The reaction was terminated by the addition of 0.3 ml of 20% trichloroacetic acid solution. Thiobarbituric acid was then added and the mixture was boiled for 10 minutes. After cooling the test tubes under running tap water, the optical density at 532 nm was measured. Lipid peroxidation in both the treated groups and the control group was expressed in nmol MDA/mg protein. The percentage inhibition indicates the anti-oxidation properties of the coumarin retinoids tested.

TABLE 6

Inhibition of I-6 and I-5 on $Fe^+$/Cys induced lipid peroxidation of rat liver microsome (n = 3)

| Group | Concentration (μM) | Lipid Peroxidation (μM MDA/mg protein) | Inhibition (%) |
|---|---|---|---|
| Control |  | 2.38 ± 0.12 |  |
| I-6 | 2 | 2.16 ± 0.18 | 8.6 |
|  | 20 | 2.13 ± 0.19 | 9.6 |
|  | 200 | 2.03 ± 0.16* | 13.5 |
| I-5 | 1 | 2.19 ± 0.13 | 7.3 |
|  | 10 | 1.95 ± 0.18* | 16.6 |
|  | 100 | 1.43 ± 0.16** | 36.6 |

*$p < 0.05$
**$p < 0.01$

EXAMPLE 18

Anti-Mutagenicity Effect of Coumarin Retinoids

An antimutagenicity assay was conducted according to the method developed by Ames et al. using *Salmonella typhimurium* strains TA 102 and TA 100 and mammalian microsomal enzymes. Beta-naphthoflavone and phenobarbital-induced rat liver supernatant (9000×g S-9 fraction) was used as the enzyme source for metabolic activation. The night before the experiment, certified bacterial solution (assessed for its biological characteristics and donated by Professor Ames) was inoculated into petri dishes. The petri dishes were then incubated for 15 hours at 37° C. From each petri dish, 0.1 ml of the bacterial solution was removed and added to sterile test tubes. To these test tubes, 0.1 ml of different concentrations of coumarin retinoids and 0.5 ml of either S-9 mixed solution or phosphate buffer were then added. The final solution for each test tube was incubated in a water bath at 37° C. for 20 minutes before adding 2 ml of agar solution. After thorough mixing, the solution was transferred into petri dishes and incubated once again at 37° C. for 48 hours. After incubation, the number of colonies in each petri dish were counted. The revertant numbers of the bacteria in control and treated groups were compared and the inhibition rate was calculated.

TABLE 7

Effect of I-6 on the induction of $His^+$/revertants by MMS mutagen (0.5 μl/plate) in *Salmonella typhimurium* strains TA100 and TA102 (n = 3)

| Group | Concentration (mg/plate) | $his^+$-revertants/per plate TA100 | Inhibition (%) | TA102 | Inhibition (%) |
|---|---|---|---|---|---|
| MMS |  | 1083.7 ± 99.3 |  | 1760 ± 288.4 |  |
| I-6 | 0.1 | 971.3 ± 102.7 | 12.8 | 1560 ± 40.0 | 13.8 |
|  | 0.5 | 947.3 ± 60.3 | 15.5 | 1375 ± 241.5 | 26.6 |

EXAMPLE 19

Effect of Coumarin Retinoids on Croton Oil Induced Ear Edema in Mice

ICR mice (body weight 18–20 grams) were used. Each group consisted of 10 mice. For the treated group, coumarin retinoids were administered at the dosage indicated in the table for 10 days. After three dosage treatments, the left ears of the mice in both the treated group and the control group were painted with 2% croton oil in 0.05 ml ether. All the mice were sacrificed six hours later and the ears of both sides were punched by a corneal knife and weighed, the difference of the ear weight of both sides for each mouse was calculated. The t-Student test was used for statistical calculation. Croton oil induced ear edema is a classical assay for evaluation of cancer promotion.

TABLE 8

Inhibition of I-10 and I-6 on croton oil induced ear edema in mice

| Groups | Dose (mg/kg) | Ear Edema (x ± SD) mg | IR (%) | P |
|---|---|---|---|---|
| Control | | 16.5 ± 1.4 | | |
| I-10 | 50 | 14.2 ± 2.3 | 14 | <0.05 |
| | 100 | 11.3 ± 3.0 | 32 | <0.01 |
| I-6 | 50 | 13.4 ± 3.1 | 19 | <0.01 |
| | 100 | 15.1 ± 2.7 | 9 | |

EXAMPLE 20

Anti-Teratogenicity Effect of Retinoids on Bone Abnormalities in Mouse Fetus

Living embryos, removed from female mice as described in Example 15, were placed in 95% ethanol until fixed, and then placed in an alizarin dye and dyed red. After the embryos became transparent, they were dissected and their skeletons were checked by observation under a microscope.

TABLE 9

Effect of I-10 on bone abnormalities in mouse fetus

| | Dosage | Delayed Calcification (%) | |
|---|---|---|---|
| Group | (mg/kg) | Occipital delay/fetus | Sternum delay/fetus |
| Control | | 0/79 | 0/79 |
| Tween 80 | 0.3% | 0/69 | 0/69 |
| I-10 | 40 | 15/81 | 21/81 |
| | 20 | 22/66 | 14/66 |
| All-trans RA | 101 | 6/16 | 16/16 |

TABLE 10

Effect of I-9 on bone abnormalities in mouse fetus

| | | Delayed Calcification (%) | |
|---|---|---|---|
| Group | Dosage (mg/kg) | Occipital number/ fetus number | Sternum number/fetus number |
| Control | — | 0/79 | 0/79 |
| Tween 80 | 0.3% | 0/69 | 0/69 |
| I-9 | 40 | 3/77 | 2/77 |
| | 20 | 0/75 | 0/75 |
| All-trans RA | 10 | 16/16 | 16/16 |

TABLE 11

Effect of II-A on Bone Abnormalities in Mouse Fetus

| | Dosage | Delayed Calcification (%) | | Cleft Palate |
|---|---|---|---|---|
| Group | (mg/kg) | Occipital | Sternum | (%) |
| Control | — | 0 | 0 | 0 |
| Solvent | — | 5.4 | 5.4 | 0 |
| II-A | 20 | 7.6 | 9.0 | 0 |
| | 40 | 7.2 | 7.2 | 0 |
| Retinoic Acid | 15 | 96.0 | 71.0 | 48 |

EXAMPLE 21

Inhibitory Effect of Coumarin Retinoids on Cancer Cells

Human cancer cell lines (KB, A2780, MCF-7, HL-60, A549) were used. For a monolayer culture, 0.5 ml of trypsin solution (0.3 gm/ml) was added to the flasks for digestion. Microtiter plates (96 well) were used for the cell culture and 200 μl of cell suspension (1200 tumor cells) were placed in each well and incubated at 37° C. for 24 hours. Following the addition of the test compound, the control and treated flasks were placed in a $CO_2$ incubator for 5 day culture. For the MTT assay, 200 μl of MTT solution (5 mg in 10 ml of phosphate buffer) plus the medium were added and incubated for another 4 hours. Following incubation, the supernatant was discarded and 200 μl of DMSO was added to each well. With a mild agitation the OD values were determined by the MR 700 Elisa at 570 nm (reference wavelength was 450 nm). The $ED_{50}$ of the compound and tumor cell survival rate $$\text{Tumor cell survival} = \frac{\text{OD of treated group}}{\text{OD of control group}}$$

as percent inhibition were calculated.

TABLE 12

Results on MTT Assay in HL-60 Cells

| Compound | Concentration (M) | Inhibition % | $ED_{50}$ (M) |
|---|---|---|---|
| I-8 | $10^{-5}$ | 63.9 ± 2.9 | $1 \times 10^{-7}$ |
| | $10^{-6}$ | 54 ± 1.9 | |
| | $10^{-7}$ | 50.5 ± 0.9 | |
| | $10^{-8}$ | 29.7 ± 1.4 | |
| I-9 | $10^{-5}$ | 61.5 ± 1.9 | $9.5 \times 10^{-7}$ |
| | $10^{-6}$ | 50.6 ± 0.5 | |
| | $10^{-7}$ | 48.8 ± 0.5 | |
| | $10^{-8}$ | 28.0 ± 5.2 | |
| I-15 | $10^{-5}$ | 54.5 ± 2.8 | $9 \times 10^{-7}$ |
| | $10^{-6}$ | 48.8 ± 1.3 | |
| | $10^{-7}$ | 34.6 ± 0.0 | |
| | $10^{-8}$ | 16.2 ± 2.4 | |
| I-21 | $10^{-5}$ | 61.2 ± 2.4 | $1 \times 10^{-6}$ |
| | $10^{-6}$ | 49.9 ± 2.5 | |
| | $10^{-7}$ | 32.5 ± 1.1 | |
| | $10^{-8}$ | 21.8 ± 3.1 | |
| I-26 | $10^{-5}$ | 68.7 ± 0.2 | $9 \times 10^{-7}$ |
| | $10^{-6}$ | 52.6 ± 0.5 | |
| | $10^{-7}$ | 43.8 ± 1.3 | |
| | $10^{-8}$ | 9.4 ± 3.7 | |
| I-5 | $10^{-5}$ | 51.6 ± 0.0 | $8.5 \times 10^{-6}$ |
| | $10^{-6}$ | 34.0 ± 7.1 | |
| | $10^{-7}$ | 11.5 ± 4.2 | |
| I-13 | $10^{-5}$ | 5.5 ± 3.9 | $>10^{-5}$ |
| | $10^{-6}$ | 4.3 ± 6.1 | |
| | $10^{-7}$ | 3.5 ± 3.9 | |

TABLE 12-continued

Results on MTT Assay in HL-60 Cells

| Compound | Concentration (M) | Inhibition % | $ED_{50}$ (M) |
|---|---|---|---|
| I-14 | $10^{-5}$ | 52.6 ± 1.3 | $9.0 \times 10^{-6}$ |
|  | $10^{-6}$ | 30.0 ± 1.4 |  |
|  | $10^{-7}$ | 10.4 ± 2.4 |  |

EXAMPLE 22

Effect of Retinoids on Growth of Chondrosarcomas in Rats

Transplantable chondrosarcomas obtained from Dr. Trown, Hoffman—La Roche Institute of Molecular Biology and Wistar rats obtained from the Breeding Center of Experimental Animals, Chinese Academy of Medical Sciences were used. According to the routine transplantation protocol as described in *Cancer Treatment Reports* 60(11) :1647–1653 (1976) where the small pieces of chondrosarcoma tumor were implanted subcutaneously in the right inguinal region of rats using a trocar. Tumor-bearing rats were randomized to a control group and a treated group. Each group consisted of ten rats. The compound was given orally for 12 days at the indicated dosage. Sixty days after transplantation, the rats were sacrificed and the tumor weight was determined. The inhibition rate was calculated according to the following formula:

$$\text{Inhibition rate} = \frac{\text{tumor weight of control} - \text{tumor weight of treated}}{\text{tumor weight of control group}} \times 100$$

TABLE 13

Effect of I-10 on the Growth of Chondrosarcoma in Rats

| Group | Animals initial | Animals final | Body Weight initial | Body Weight final | Tumor Weight (grams) | Inhibition rate (%) |
|---|---|---|---|---|---|---|
| Control | 10 | 10 | 95.4 | 251.0 | 14.2 |  |
| Treated # 5 mg/kg | 10 | 10 | 97.8 | 258.4 | 12.1 | 14.8 |
| 10 mg/kg | 10 | 9 | 98.2 | 248.0 | 12.8 | 9.8 |
| 20 mg/kg | 10 | 9 | 97.4 | 253.1 | 8.2 | 42.2* |

P.O. Administration - - *P < 0.05

TABLE 14

Effect of II-A on the Growth of Chondrosarcoma in Rats

| Group | Animals initial | Animals final | Body Weight initial | Body Weight final | Tumor Weight (grams) | Inhibition rate (%) |
|---|---|---|---|---|---|---|
| Control | 10 | 10 | 70.6 | 218.8 | 10.7 |  |
| 2 mg/kg ×10 | 10 | 9 | 74.1 | 130.6 | 5.4 | 49.5 |
| 5 mg/kg ×10 | 10 | 9 | 71.7 | 129.2 | 4.0 | 62.6 |

EXAMPLE 23

Effect of Retinoids on Cancer Cell Differentiation and Cancer Cell Survival

The protocols of Examples 14 and 21 were used, for the NBT and MTT assays, respectively.

TABLE 15

Effect of Coumarin retinoids on HL-60 cells

| Compound | NBT $ED_{50}$ | MTT (mol/L) |
|---|---|---|
| I-28 | $>10^{-5}$ | $>10^{-5}$ |
| I-29 | $>10^{-5}$ | $1.9 \times 10^{-6}$ |
| I-30 | $>10^{-5}$ | $>10^{-5}$ |
| I-31 | $>10^{-5}$ | $>10^{-5}$ |
| I-32 | $1.3 \times 10^{-5}$ | $1.1 \times 10^{-5}$ |
| I-33 | $>10^{-5}$ | $3.2 \times 10^{-6}$ |
| I-34 | $>10^{-5}$ | $>10^{-5}$ |
| I-35 | $6.7 \times 10^{-6}$ | $2.6 \times 10^{-6}$ |
| I-36 | $>10^{-5}$ | $3.2 \times 10^{-6}$ |

TABLE 16

Effect of purine retinoid compounds on HL-60, HCT-8, A2780, KB and BEL 7402 cell lines

| Comp. | NBT (mol/L) HL-60 | MTT $ED_{50}$ (mol/L) HCT-8 | A2780 | KB | Bel7402 |
|---|---|---|---|---|---|
| II-D | $>10^{-5}$ | $4 \times >10^{-6}$ | $>10^{-5}$ | $>10^{-5}$ | $5 \times 10^{-6}$ |
| II-F | $>10^{-5}$ | $>10^{-5}$ | $>10^{-5}$ | $>10^{-5}$ | $>10^{-5}$ |

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A compound selected from the group consisting of 3-Acetyl-5-methyl-7-retinoyloxy-coumarin, 3-Acetyl-7-retinoyloxy-8-methyl-coumarin, 3-Acetyl-5-carboxy-7-retinoyloxy-coumarin, 3-Acetyl 7-retinoyloxy-8-carboxy coumarin, 3-Acetyl-6-chloro-7-retinoyloxy-coumarin, 3-Acetyl-5-retinoyloxy-methylene-7-retinoyloxy-coumarin, 3-Acetyl-5-retinoyloxy-6-carboxy-coumarin, 3-Acetyl-7,8-diretinoyloxy-coumarin, 3-Acetyl-5,7-diretinoyloxy-coumarin, 3-Acetyl-5-ethoxycarbo-7-retinoyloxy-coumarin, 3-Ethoxycarbo-5-dodecoxycarbo-7,8-retinoyloxy-coumarin, 3-Acetyl-6-ethyl-7-retinoyloxy-coumarin, 3-Acetyl-6-hexyl-7-retinoyloxy-coumarin, 3-Ethoxycarbo-7-retinoyloxy-8-methyl-coumarin, 3,6-Diacetyl-7-retinoyloxy-coumarin, 3-Ethoxycarbo-7-retinoyloxy-coumarin, 3-Ethoxycarbo-6-chloro07-retinoyloxy-coumarin, 3-Ethoxycarbo-5-carboxy-7-retinoyloxy-coumarin, 3-Ethoxycarbo-7,8-diretinoyloxy-coumarin, 3-Ethoxycarbo-5,7-diretinoyloxy-coumarin, 3-Ethoxycarbo-6-ethyl-7-retinoyloxy-coumarin, 3-Ethoxycarbo-7-retinoyloxy-8-acetyl-coumarin, 3-Ethoxycarbo-5-retinoyloxy-6-benzoyl-coumarin, 3-Carboxy-6-hexyl-7-retinoyloxy-coumarin, 3-Carbamoyl-5-carboxy 7-retinoyloxy-coumarin, 3-Carbamoyl-6-chloro-7-retinoyloxy-coumarin, 4-Retinoyloxy-6-t-butyl-coumarin, 4-Retinoyloxy-8-methyl-coumarin, 4,8-Dimethyl-7-retinoyloxy-coumarin, 4-Methyl-6-ethyl-7-retinoyloxy coumarin, 4-Methyl-7-retinoyloxy-coumarin, 4-Methyl-5,7-retinoyloxy-coumarin, 4-Methyl-6-hexyl-7-retinoyloxy-coumarin, 4-Retinoyloxy-6-methyl-coumarin, 4-Methyl-7,8-diretinoyloxy-coumarin, 4-retinoyloxy-7-methyl-coumarin, and 4-retinoyloxy-coumarin.

2. A compound according to claim 1, wherein said compound is 3-Acetyl-7,8-diretinoyloxy-coumarin.

3. A pharmaceutical composition comprising a compound according to claim 1, and a pharmaceutically acceptable carrier.

4. A pharmaceutical composition according to claim 3, further comprising a drug selected from an anti-cancer compound or composition or an immunomodulator.

5. A method for inhibiting precancer or cancer-related pathology in cells or tissue of a mammal, comprising the step of administering an effective precancer or cancer inhibiting amount of a compound according to claim 1.

* * * * *

UNITED STATES PATENT AND TRADEMARK OFFICE
CERTIFICATE OF CORRECTION

PATENT NO. : 5,716,982
DATED : Feb. 10, 1998
INVENTOR(S) : Han et al.

It is certified that error appears in the above-identified patent and that said Letters Patent is hereby corrected as shown below:

Column 1, line 59, (spec. page 3, line 6), delete "retinic" and insert therefor --retinoic--;

Column 1, line 60, (spec. page 3, line 6), delete "retinic" and insert therefor ---retinoic--;

Column 1, line 62, (spec. page 3, line 8), delete "retinic" and insert therefor --retinoic--;

Column 8, line 11, (spec. page 14, line 23), delete "anglogenesis" and insert therefor --angiogenesis--;

Signed and Sealed this

Twenty-ninth Day of September, 1998

Attest:

BRUCE LEHMAN

*Attesting Officer*    *Commissioner of Patents and Trademarks*